(12) United States Patent
Castelijns et al.

(10) Patent No.: US 8,598,303 B2
(45) Date of Patent: Dec. 3, 2013

(54) PROCESS TO PRODUCE VALEROLACTONE FROM LEVULINIC ACID

(75) Inventors: Anna Maria Cornelia Francisca Castelijns, Echt (NL); Michele Catherine Christianne Janssen, Echt (NL); Henricus Wilhemus Leonardus Marie Vaessen, Echt (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 13/528,281

(22) Filed: Jun. 20, 2012

(65) Prior Publication Data

US 2012/0329981 A1    Dec. 27, 2012

Related U.S. Application Data

(60) Provisional application No. 61/499,438, filed on Jun. 21, 2011.

(30) Foreign Application Priority Data

Jun. 21, 2011    (EP) .................................... 11170809

(51) Int. Cl.
*C07C 67/38* (2006.01)

(52) U.S. Cl.
USPC ........ 528/335; 428/847.1; 528/125; 528/126; 528/310; 549/273; 560/204; 560/212

(58) Field of Classification Search
USPC ............ 528/335; 549/326; 562/515; 585/324
See application file for complete search history.

(56) References Cited

U.S. PATENT DOCUMENTS

| | | | | |
|---|---|---|---|---|
| 5,883,266 A | * | 3/1999 | Elliott et al. | 549/273 |
| 2003/0055270 A1 | | 3/2003 | Manzer | |
| 2010/0324310 A1 | * | 12/2010 | Dumesic et al. | 549/326 |
| 2011/0237806 A1 | * | 9/2011 | Pinkos et al. | 549/273 |

OTHER PUBLICATIONS

Fabre et al (Catalytic Hydrogenation of Arabinonic Acid and Lactones to Arabitol, Journal of Catalysis 208, 247-254 (Mar. 2002).*
Extended European Search Report for EP-11 17 0809; Completed Sep. 9, 2011.
Mehdl et al., "Integration of Homogeneous and Heterogeneous Catalytic Processes for a Multi-Step Conversion of Biomass: From Sucrose to Levulinic Acid, [Gamma]-Valerolactone, 1-4-Pentanediol, 2-Methyl-Tetrahydrofuran, and Alkanes," Topics in Catalysis, vol. 48, No. 1-4, pp. 49-54, (Apr. 5, 2008).
Chalid et al.; "Experimental and Kinetic Modeling Studies on the Biphasic Hydrogenation of Levulinic Acid to [Gamma]-Valerolactone Using a Homogeneous Water-Soluble Ru-(TPPTS) Catalyst," Journal of Molecular Catalysis A: Chemical, vol. 341, No. 1-2, pp. 14-21, (May 1, 2011).

* cited by examiner

*Primary Examiner* — Gregory Listvoyb
(74) *Attorney, Agent, or Firm* — Miles & Stockbridge, P.C.

(57) ABSTRACT

The invention provides a process for the preparation of valerolactone, said process comprising reacting levulinic acid with hydrogen by using a solid Ru catalyst, characterized in that the process is carried out in the presence of at least 0.08% (w/w) water relative to the amount of levulinic acid. Said process may be faster and more selective. This process advantageously allows the production of valerolactone from renewable sources.

The valerolactone may be used in the preparation of methylpentenoate, adipic acid dimethylester, adipic acid, hexamethylenediamine, and polyamide 6,6 (all claimed).

19 Claims, No Drawings

PROCESS TO PRODUCE VALEROLACTONE FROM LEVULINIC ACID

CROSS REFERENCE TO RELATED APPLICATIONS

This application claims priority to European Application No. 11170809.5, filed Jun. 21, 2011, and U.S. Provisional Application No. 61/499,438, filed Jun. 21, 2011, both of which are incorporated herein by reference in their entireties.

BACKGROUND OF THE INVENTION

1. Field of the Invention

The present invention relates to a process for the production of valerolactone.

2. Description of Related Art

Gamma-valerolactone (5-methylbutyrolactone, in the context of the invention also referred to as "valerolactone") is a valuable compound which is inter alia used in the production of adipic acid (1,6-hexanedioic acid) which is an important precursor for inter alia the production of polyamides such as polyamide 6,6 (also referred to as "Nylon") or polyamide 4,6 (also referred to as "Stanyl"). Further, esters of adipic acid may be used in plasticisers, lubricants, solvents and in a variety of polyurethane resins. Other uses of adipic acid are as food acidulants, applications in adhesives, insecticides, tanning and dyeing.

The most important process to produce adipic acid is based on oil and starts from benzene. A disadvantage of this process is that it is based on fossil derived oil and is therefore not renewable. Another disadvantage is the evolution of NOx during the oxidation step, which either is vented to the air, which is highly undesirable as it is a greenhouse gas, or its catalytically destroyed, which is an expensive process.

New processes for the production of adipic acid have been developed based on butadiene. However, such processes are also environmentally unfavourable.

A third production route to produce adipic acid involves the use of valerolactone which can be converted to methylpentenoates in the presence of an acidic or basic catalyst in the gas phase or in the liquid phase. Methylpentenoate can be converted to dimethyladipate in an alkoxycarbonylation reaction which dimethyladipate can be converted to adipic acid in a simple hydrolysis reaction. The use of valerolactone in the production of adipic acid is environmentally advantageous since it can be produced from levulinic acid, which in turn can be produced from renewable sources such as plant waste.

US2003/0055270 discloses a process to produce valerolactone from levulinic acid using a solid Ru catalyst, e.g. supported on carbon. A problem of the process as described by US2003/0055270 is that the selectivity towards valerolactone is insufficient. Another problem of process as described by US2003/0055270 is that the conversion yield is insufficient. The use of valerolactone in the production of adipic acid is environmentally advantageous since it can be produced from levulinic acid, which in turn can be produced from renewable sources such as plant waste.

BRIEF SUMMARY OF THE INVENTION

Therefore, the present invention provides a process for the preparation of valerolactone, said process comprising reacting levulinic acid with hydrogen by using a solid Ru catalyst, characterised in that the process is carried out in the presence of at least 0.08% (w/w) water relative to the amount of levulinic acid.

The amount of water is expressed relative to the amount of initial levulinic acid, i.e. the amount of levulinic acid at the start of the process when no or hardly any levulinic acid has been converted. The amount of levulinic acid can be determined e.g. by GC.

The process of the invention involves a hydrogenation reaction. The Ru catalyst is preferably present in a catalytic amount and is suitable for hydrogenation of ketones. Preferably the Ru catalyst is supported on a support medium, for example on carbon or alumina. However, Ru oxide (RuO) can also be used.

The inventors surprisingly found that reacting levulinic acid with hydrogen by using a solid Ru catalyst, whereby the process is carried out in the presence of at least 0.08% (w/w) water relative to the amount of levulinic acid, a high production capacity and/or a high conversion yield and/or a high selectivity may be realised in the production of valerolactone. In contrast, the conversion of levulinic acid to valerolactone using a solid Ru catalyst as carried out in US2003/0055270 is done without the addition of any water. In fact, in US2003/0055270 it is described that the catalyst is dried at 400° C. for 2 hours prior to the process.

DETAILED DESCRIPTION OF THE INVENTION

That reacting levulinic acid with hydrogen by using a solid Ru catalyst in the presence of at least 0.08% (w/w) water relative to the amount of levulinic acid results in high conversion yield and/or a high selectivity is all the more surprising since said reaction involves the production of condensation water. As the reaction proceeds, the amount of water in the process increases. Nevertheless, it appears that the condensation water which builds up during the course of the reaction does not impart the same effect with respect to reaction velocity and/or selectivity as does the initial presence of at least 0.08% w/w water, i.e. the initial presence of at least 0.08% w/w water in the process is essential.

The amount of water in the process of the invention is preferably at least 0.1% w/w, more preferably at least 0.2%, at least 0.3%, at least 0.4% w/w, more preferably at least 0.5%, at least 0.75% w/w, more preferably at least 1%, at least 1.3%, at least 1.5% w/w, even more preferably at least 1.7%, at least 2%, at least 2.5% w/w, all relative to the amount of levulinic acid. The upper limit of the amount of water is less critical. However, if the amount of water is too high, the substrate and/or catalyst may be diluted such that the reaction velocity or productivity may decrease which is undesired. Therefore, the amount of water in the process of the invention is preferably less than 10% w/w, more preferably less than 8% w/w, less than 6% w/w, less than 5% w/w, all relative to the amount of levulinic acid.

The water which is present in the process of invention may be added separately, or added as part of one or more of the components, or both. For example, it may be added to the process in the form of liquid water or in the form of steam. It may also be present in the form of crystal water. The water may also be added to process together with one or more of the reaction components, e.g. as part of the levulinic acid or the Ru catalyst or both. The water may also be added first and the other reaction components are added later. Reaction components such as levulinic acid and the catalyst may also be added first, and the water may be added subsequently. Other ways of adding water are also possible, such as first adding levulinic acid, then adding water, and subsequently adding the Ru catalyst, or first adding the Ru catalyst, then adding water and finally adding levulinic acid. If the catalyst and/or the levulinic acid happens to contain trace amounts of water, it may be preferred to first measure the water content of these reaction components, e.g. by Karl Fischer titration, such that the suitable amount of water to be added can be calculated in order to arrive at the desired water content in the process.

The temperature at which the process of the invention is carried out is not critical and may be anywhere between 100 and 250° C., more preferably between 100 and 200° C. Preferably a temperature of between 100 and 150° C. is used because it seems that the highest selectivity can be obtained in this temperature range. Lower temperatures are also desired due to cost considerations and equipment requirements.

The pressure at which the process of the invention is carried out is also not critical, but it may be advantageous to carry out the process at lower pressure, e.g. less than 4.8 MPa. Preferably the pressure is between 1 and 4 MPa, more preferably between 1 and 3 MPa, even more preferably between 1 and 2.5 MPa, even more preferably between 1 and 2.2 MPa.

The amount of catalyst to be used is not critical. Preferably the amount of catalyst is between 2.5 and 2,000 ppm Ru relative to the initial amount of levulinic acid present in the reaction mixture, i.e. the amount of levulinic acid which is present in the reaction mixture at the start of the reaction when no or hardly any levulinic acid has been converted. More preferably the amount of catalyst is between 5 and 1,000 ppm Ru, even more preferably between 10 and 500 ppm Ru, all relative to the initial amount of levulinic acid. The process of the invention may advantageously be done at low (e.g. less than 500 ppm Ru) catalyst concentrations whilst yielding good selectivity.

The effect of at least 0.08% w/w water relative to the amount of levulinic acid may be stronger at lower amounts catalyst. In other words, the presence at least 0.08% w/w water relative to the amount of levulinic acid may be more important, and indeed may even be required for the hydrogenation reaction to proceed at all when a low amount of catalyst is selected, for instance for economic reasons.

Ru catalysts such as Ru/C or Ru—$Al_2O_3$ are commercially available and the amount of Ru and any support are usually labeled. In case the amount of Ru is not given, the skilled person knows how to determine the amount of Ru, for example by atomic absorption spectrometry or plasma emission spectrometry.

The process of the invention may be carried in the absence of a solvent. In the context of the invention a solvent is understood to be added to the reaction mixture, i.e. in the meaning of the invention the reaction product is not considered a solvent. The absence of a solvent may advantageously result in higher conversion and/or selectivity and may be preferred for economic reasons.

The levulinic acid may be produced from renewable sources. A suitable example of renewable sources is plant material, particularly plant waste. Plant material usually contains carbohydrates that can serve as a starting molecule for the production of levulinic acid. For example, levulinic acid can be prepared by converting a C6 carbohydrate to levulinic acid in an acid-catalysed reaction. Such processes are for example described in U.S. Pat. No. 3,065,263; B. Girisuta et al., Chem. Eng. Res. Des. 2006, 84, 339-349; B. F. M. Kuster et al., Carbohydr. Res., 1977, 54, 165-176; WO89/10362; and WO96/40609. Examples of C6 carbohydrates are glucose, fructose, mannose and galactose. Preferred raw material for the C6 carbohydrates is lignocellulosic material containing carbohydrate based polymers composed partly or entirely from C6 sugars such as lignocellulose, cellulose, starch and hemicellulose. The C6 carbohydrate may comprise other components, such as plant waste, sewage etc.

The invention may be particularly useful since it allows for economically feasible production of valerolactone, and also of derivatives thereof such as methylpentenoate, adipic acid dimethylester, adipic acid, hexamethylenediamine, and polyamide 6,6, all produced via or from renewable sources. One such a suitable renewable source is plant material, which can be converted into levulinic acid. Although the production of valerolactone from levulinic acid is known from US2003/0055270, the process conditions as described in US2003/0055270 and/or conversion yield and/or selectivity resulting from said process may form a barrier for the economic feasibility of said process. The process of US2003/0055270 suffers from low conversion yield (usually less than 100%, often even less than 80% and even as low as 32%), low selectivity (less than 98.5%, occasionally even as low as 67.7%), is done at high process temperature (215° C.) and high pressure (4.8 MPa), makes use of a solvent (dioxane) and high catalyst concentrations. For example, the amount of Ru/C used in Table 1 of US2003/0055270 typically ranges between 2% and 20% (w/w) relative to the amount of levulinic acid, which corresponds to a range of between approximately 1000 and 10,000 ppm Ru relative to the amount of levulinic acid, respectively. Low catalyst concentrations (such as for instance less than 1000 ppm Ru) are usually economically desirable, but the selectivity in the process as described in US2003/0055270 appears to be lower at lower catalyst concentrations. Said barriers can be overcome by the process of the invention.

The invention further provides a process to produce methylpentenoate comprising converting valerolactone produced by the process of the invention into methylpentenoate by treatment with methanol in the presence of an acidic or basic catalyst. The conversion of valerolactone to methyl pentenoate can be done either in the liquid phase or in the gas phase, and is inter alia described in WO 2005/058793, WO02004/007421, and U.S. Pat. No. 4,740,613.

The invention also provides a process to prepare adipic acid dimethylester comprising converting methylpentenoate produced in the process of the invention by treatment with a catalyst, CO and methanol. Such an alkoxycarbonylation reaction is described by e.g. WO2001/068583.

The invention also provides a process to prepare adipic acid comprising converting adipic acid dimethylester produced in the process of the invention to adipic acid in a hydrolysis reaction. The hydrolysis of adipic acid dimethylester to adipic acid is well known to the person skilled in the art. The hydrolysis is preferably catalysed by an acidic catalyst.

The invention also provides a process to prepare ammonium adipate comprising converting adipic acid produced by the process of the invention to ammonium adipate by treatment with ammonia.

The invention also provides a process to prepare adiponitrile comprising converting ammonium adipate produced in the process of the invention into adiponitrile in a dehydration reaction.

The invention also provides a process to prepare hexamethylenediamine comprising converting adiponitrile produced of the process of the invention into hexamethylenediamine in a reduction reaction.

The invention also provides a process to produce polyamide 6,6 by converting adipic acid, preferably adipic acid produced in a process according of the invention with hexamethylenediamine, preferably hexamethylenediamine produced by a process of the invention, in a polymerization reaction. Polyamide 6,6 produced by the invention, particularly polyamide 6,6 produced from adipic acid and hexamethylenediamine produced by a process of the invention may be advantageously environmentally sustainable.

The invention will be further elucidated with reference to the following examples, without however being limited thereto.

Example 1

Hydrogenation of Levulinic Acid to γ-Valerolactone

Levulinic acid was obtained from Acros Organics, Geel, Belgium. Valerolactone was measured by GC analysis using cyclohexylbenzene as an external standard. Escat 4401, CAS [7440-18-8] (reduced) containing 5% Ru/C (Ru:C ratio, 1:20) and 58.45% water, was purchased form Strem Chemicals, Newburyport, Mass., USA. Dry Ru/C CAS [7440-18-8] containing 5% Ru/C (Ru:C 1:20) was also purchased from Strem Chemicals, Newburyport, Mass., USA.

A 150 mL autoclave (Parr Instrument Company, Moline, Ill., USA) was charged with levulinic acid (80 g, 0.68 mol) and Ru/C catalyst (see Table 1). The ratio Ru:C in the catalyst was 1:20 based on dry weight. Water was added to the reaction mixture such as to obtain a total amount of water in the reaction mixture as shown in Table 1. The actual total water content was measured by means of Karl Fisher titration and is expressed as % (w/w) relative to the total weight of the reaction mixture. Then the autoclave was purged 3 times with nitrogen and subsequently 3 times with hydrogen. The autoclave was heated to 130° C. and pressurized to 2.06 MPa hydrogen. Samples were taken in time. Results see Table 1.

TABLE 1

Results hydrogenation of levulinic acid to γ-valerolactone

| Entry | Catalyst | Ru/C (mg) | Total water content (wt %) | Reaction time (h) | Conversion (%) | Selectivity to VL (%) |
|---|---|---|---|---|---|---|
| 1 | Escat 4401 (58.45% water) | 800 | 0.75 | 1 | 60 | >99 |
| 2 | Escat 4401 (58.45% water) | 800 | 1.72 | 1 | 79 | >99 |
| 3 | Dry Ru/C | 41.3 | 0.08 | 49.5 | 51 | >99 |
| 4 | Dry Ru/C | 41.3 | 1.29 | 48 | 59 | >99 |
| 5 | Dry Ru/C | 41.3 | 2.47 | 48 | 73 | >99 |

The invention claimed is:

1. A process for the preparation of valerolactone, said process comprising reacting levulinic acid with hydrogen by using a solid Ru catalyst, wherein the process is carried out in the presence of 0.08% to 10% (w/w) water relative to the amount of levulinic acid.

2. The process of claim 1, wherein the amount of water in the reaction is at least 1% (w/w) relative to the amount of levulinic acid.

3. The process of claim 1, wherein the amount of water in the reaction is at least 2.5% (w/w) relative to the amount of levulinic acid.

4. The process of claim 1, wherein the reaction is carried out at a temperature of from 100 to 150° C.

5. The process of claim 1, wherein the reaction is carried out at a pressure of from 1 to 4 MPa.

6. The process of claim 1, wherein amount of said Ru catalyst is from 10 to 500 ppm Ru relative to the amount of initial levulinic acid.

7. The process of claim 1, wherein said process is carried out in the absence of a solvent.

8. The process of claim 1, wherein levulinic acid is prepared by converting a C6 carbohydrate to levulinic acid in an acid-catalysed reaction.

9. A process for the preparation of methylpentenoate comprising converting valerolactone produced by said process of claim 1 into methylpentenoate by treatment with methanol in the presence of an acidic or basic catalyst.

10. A process for the preparation of adipic acid dimethylester comprising converting methylpentenoate produced in said process of claim 9 by treatment with a catalyst, CO and methanol.

11. A process for the preparation of adipic acid comprising converting adipic acid dimethylester produced in said process of claim 10 to adipic acid in a hydrolysis reaction.

12. A process to prepare ammonium adipate comprising converting adipic acid produced by said process of claim 11 into ammonium adipate by treatment with ammonia.

13. A process for the preparation of adiponitrile comprising converting ammonium adipate produced in said process of claim 12 into adiponitrile in a dehydration reaction.

14. A process for the preparation of hexamethylenediamine comprising converting adiponitrile produced in said process of claim 13 into hexamethylenediamine in a reduction reaction.

15. A process for the production of polyamide 6,6 by converting adipic acid produced in said process of claim 11 with hexamethylenediamine in a polymerization reaction.

16. The process of claim 15, wherein the hexamethylenediamine is obtained by:
  (a) preparing valerolactone by reacting levulinic acid with hydrogen by using a solid Ru catalyst, wherein the process is carried out in the presence of 0.08% to 10% (w/w) water relative to the amount of levulinic acid;
  (b) converting the valerolactone into methylpentenoate by treatment with methanol in the presence of an acidic or basic catalyst;
  (c) converting the methylpentenoate into adipic acid dimethylester by treatment with a catalyst, CO and methanol;
  (d) converting the adipic acid dimethylester to adipic acid in a hydrolysis reaction;
  (e) converting the adipic acid into ammonium adipate by treatment with ammonia;
  (f) converting the ammonium adipate into adiponitrile in a dehydration reaction; and
  (g) converting the adiponitrile into hexamethylenediamine in a reduction reaction.

17. The process of claim 1, wherein the amount of water in the process is less than 8% (w/w) relative to the amount of levulinic acid.

18. The process of claim 1, wherein the amount of water in the process is less than 6% (w/w) relative to the amount of levulinic acid.

19. The process of claim 1, wherein the amount of water in the process is less than 5% (w/w) relative to the amount of levulinic acid.

* * * * *